(12) United States Patent
Takahashi et al.

(10) Patent No.: US 9,803,031 B2
(45) Date of Patent: Oct. 31, 2017

(54) MODIFIED POLYMER, RUBBER COMPOSITION AND PNEUMATIC TIRE

(71) Applicant: THE YOKOHAMA RUBBER CO., LTD., Minato-ku, Tokyo (JP)

(72) Inventors: Ryota Takahashi, Hiratsuka (JP); Manabu Kato, Hiratsuka (JP); Takahiro Okamatsu, Hiratsuka (JP); Yoshiaki Kirino, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 15/115,171

(22) PCT Filed: Dec. 22, 2014

(86) PCT No.: PCT/JP2014/083980
§ 371 (c)(1),
(2) Date: Jul. 28, 2016

(87) PCT Pub. No.: WO2015/114997
PCT Pub. Date: Aug. 6, 2015

(65) Prior Publication Data
US 2016/0340446 A1    Nov. 24, 2016

(30) Foreign Application Priority Data

Jan. 31, 2014 (JP) .................. 2014-016763
Jan. 31, 2014 (JP) .................. 2014-016820

(51) Int. Cl.
*C08C 19/22* (2006.01)
*B60C 1/00* (2006.01)
(Continued)

(52) U.S. Cl.
CPC ............ *C08C 19/22* (2013.01); *B60C 1/0016* (2013.01); *C07C 251/48* (2013.01);
(Continued)

(58) Field of Classification Search
CPC ..... C08C 19/22; B60C 1/0016; C07C 251/48; C07D 213/53; C07D 233/64; C08K 3/36; C08L 7/00; C08L 9/06; C08L 2205/025
(Continued)

(56) References Cited

U.S. PATENT DOCUMENTS 3,792,031 A    2/1974    Udding
2006/0084730 A1    4/2006    Fukushima et al.
(Continued)

FOREIGN PATENT DOCUMENTS

JP    47-025712 B1    7/1972
JP    48-016996 A    3/1973
(Continued)

*Primary Examiner* — Ling Choi
*Assistant Examiner* — Ronald Grinsted
(74) *Attorney, Agent, or Firm* — Carrier Blackman & Associates, P.C.; Joseph P. Carrier; Anne G. Sabourin

(57) ABSTRACT

The purpose of the present invention is to provide a modified polymer that significantly reduces heat build-up due to the modification when the modified polymer is formed into a rubber composition, a rubber composition containing the modified polymer, and a pneumatic tire in which the rubber composition is used. The modified polymer of the present invention is a modified polymer obtained by modifying a styrene-conjugated diene copolymer (A) with a nitrone compound (B). In the modified polymer, the content of styrene units in the styrene-conjugated diene copolymer (A) is 10% by mass or greater, and the proportion of vinyl bonds among all the double bonds contained in the styrene-conjugated diene copolymer (A) is 5 mol % or greater.

13 Claims, 1 Drawing Sheet

(51) Int. Cl.
  *C07C 251/48*  (2006.01)
  *C07D 213/53*  (2006.01)
  *C07D 233/64*  (2006.01)
  *C08K 3/36*  (2006.01)
  *C08L 7/00*  (2006.01)
  *C08L 9/06*  (2006.01)

(52) U.S. Cl.
  CPC ......... *C07D 213/53* (2013.01); *C07D 233/64* (2013.01); *C08K 3/36* (2013.01); *C08L 7/00* (2013.01); *C08L 9/06* (2013.01); *C08L 2205/025* (2013.01)

(58) Field of Classification Search
  USPC ........................................................ 524/526
  See application file for complete search history.

(56) References Cited

U.S. PATENT DOCUMENTS

2007/0004869 A1* 1/2007 Parker .................. B60C 1/0016
   525/331.9
2015/0322190 A1  11/2015 Takahashi et al.

FOREIGN PATENT DOCUMENTS

| JP | 2007-070439 A | 3/2007 |
| JP | 2008-517071 A | 5/2008 |
| JP | 2013-032471 A | 2/2013 |
| WO | 2014/077364 A1 | 5/2014 |

\* cited by examiner

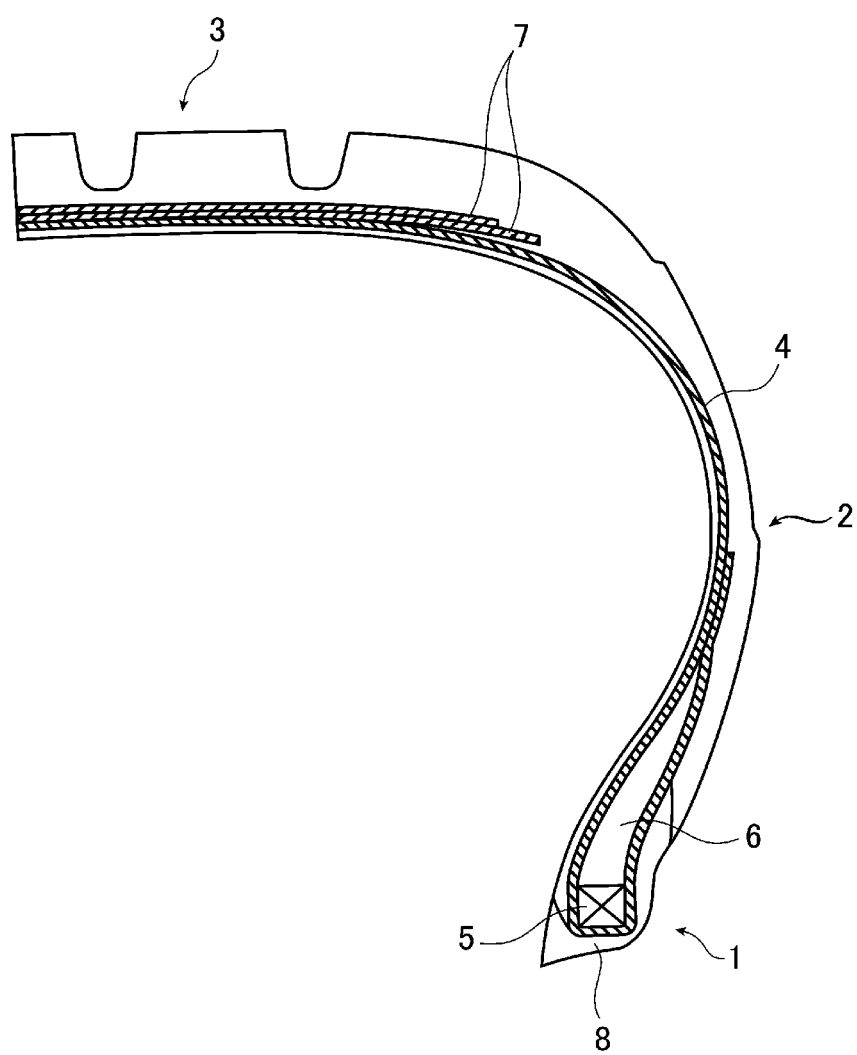

MODIFIED POLYMER, RUBBER COMPOSITION AND PNEUMATIC TIRE

TECHNICAL FIELD

The present invention relates to a modified polymer, a rubber composition containing the modified polymer, and a pneumatic tire in which the rubber composition is used.

BACKGROUND ART

Modified polymers that are modified with compounds having nitrone groups (nitrone compounds) have been known conventionally as polymers contained in rubber compositions for use in tires and the like.

For example, claim 1 of Patent Document 1 discloses "a rubber composition comprising from 10 to 120 parts by weight of silica per 100 parts by weight of diene-based rubber containing from 5 to 100% by weight of modified butadiene rubber, the modified butadiene rubber being obtained by modifying a butadiene rubber having a cis-content of 90% or greater with a nitrone compound having a nitrogen-containing heterocycle in a molecule." Patent Document 1 discloses that heat build-up is reduced by modification using a nitrone compound.

CITATION LIST

Patent Literature

Patent Document 1: Japanese Unexamined Patent Application Publication No. 2013-032471A

SUMMARY OF INVENTION

Technical Problem

Recently, from the perspective of environmental problems, further enhancement of fuel consumption performance during traveling via vehicle has been required, and along with such a requirement, further reduction in heat build-up due to modification has been demanded.

Under such circumstances, when the inventors of the present invention prepared a rubber composition using a polymer that was modified with a nitrone compound in accordance with Patent Document 1, cases where reduction in heat build-up via such modification was small were observed and thus it was found that the rubber composition does not always achieve the level that is demanded recently.

Therefore, in light of the circumstances describe above, an object of the present invention is to provide a modified polymer that significantly reduces heat build-up via the modification when the modified polymer is formed into a rubber composition, a rubber composition containing the modified polymer, and a pneumatic tire in which the rubber composition is used.

Solution to Problem

As a result of diligent research to solve the above problems, the inventors of the present invention have found that use of a styrene-conjugated diene copolymer having a specific structure as a polymer that is modified with a nitrone compound can significantly reduce the heat build-up due to the modification when a rubber composition is formed, and thus completed the present invention.

Specifically, the inventors discovered that the problems described above can be solved by the following features.

(1) A modified polymer obtained by modifying a styrene-conjugated diene copolymer (A) with a nitrone compound (B);

a content of styrene units in the styrene-conjugated diene copolymer (A) being 10% by mass or greater; and a proportion of vinyl bonds among all the double bonds contained in the styrene-conjugated diene copolymer (A) being 5 mol % or greater.

(2) The modified polymer according to (1) described above, wherein the nitrone compound (B) has a carboxy group.

(3) The modified polymer according to (1) or (2) described above, wherein the nitrone compound (B) is N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, or N-(2-carboxyphenyl)-α-phenylnitrone.

(4) The modified polymer according to any one of (1) to (3) described above, wherein the styrene-conjugated diene copolymer (A) is a styrene-butadiene rubber.

(5) A rubber composition comprising the modified polymer described in any one of (1) to (4) described above.

(6) The rubber composition according to (5) described above, further comprising a diene-based rubber except the modified polymer.

(7) The rubber composition according to (6) described above, wherein the diene-based rubber except the modified polymer is at least one type selected from the group consisting of butadiene rubbers, aromatic vinyl-conjugated diene copolymers, and natural rubbers.

(8) The rubber composition according to (7) described above, wherein a mass ratio of the modified polymer to the butadiene rubber (modified polymer/butadiene rubber) is from 95/5 to 68/32.

(9) The rubber composition according to (7) or (8) described above, wherein a mass ratio of the modified polymer to the aromatic vinyl-conjugated diene copolymer [(modified polymer)/(aromatic vinyl-conjugated diene copolymer)] is (10 or greater)/(90 or less).

(10) The rubber composition according to any one of (7) to (9) described above, wherein a mass ratio of the butadiene rubber to the natural rubber (butadiene rubber/natural rubber) is from 20/80 to 70/30.

(11) The rubber composition according to any one of (6) to (10) described above, wherein a content of the modified polymer is 10 parts by mass or greater per 100 parts by mass total of a content of the modified polymer and a content of the diene-based rubber except the modified polymer.

(12) The rubber composition according to any one of (5) to (11) described above, further comprising silica.

(13) The rubber composition according to (12) described above, wherein a content of the silica is from 8 to 130 parts by mass per 100 parts by mass total of a content of the modified polymer and a content of the diene-based rubber except the modified polymer.

(14) A pneumatic tire comprising the rubber composition described in any one of (5) to (13) described above.

Furthermore, the inventors of the present invention have found that rubber compositions of [1] to [10] below that contain a styrene-butadiene rubber modified with the nitrone compound (B) described above (modifier having a nitrone group), a butadiene rubber, and silica, and a pneumatic tire of [11] exhibit high elongation at break and excellent low heat build-up.

[1] A rubber composition comprising: a modified polymer produced by reacting a nitrone compound (B) (modifier having a nitrone group) to a double bond contained in a styrene-butadiene rubber; a diene-based rubber containing a butadiene rubber; and silica;

a mass ratio of the modified polymer to the butadiene rubber (modified polymer/butadiene rubber) being from 95/5 to 68/32.

[2] The rubber composition according to [1] described above, wherein the modifier further contains a carboxy group.

[3] The rubber composition according to [1] or [2] described above, wherein the modifier is at least one type of compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-αphenylnitrone, N-(3-carboxyphenyl)-α-phenylnitrone, and N-(2-carboxyphenyl)-α-phenylnitrone.

[4] The rubber composition according to any one of [1] to [3] described above, wherein an amount of the modifier is from 0.01 to 2.0 mol % of the double bonds contained in the styrene-butadiene rubber.

[5] The rubber composition according to any one of [1] to [4] described above, wherein the amount of the modifier introduced to the modified polymer is from 0.1 parts by mass to 10 parts by mass per 100 parts by mass of the diene-based rubber.

[6] The rubber composition according to any one of [1] to [5] described above, wherein an amount of styrene contained in the styrene-butadiene rubber is 10% by mass (% by weight) or greater in the styrene-butadiene rubber.

[7] The rubber composition according to any one of [1] to [6] described above, wherein the diene-based rubber further contains an aromatic vinyl-conjugated diene copolymer (except the modified polymer), and a mass ratio of the modified polymer to the aromatic vinyl-conjugated diene copolymer [(modified polymer)/(aromatic vinyl-conjugated diene copolymer)] is (10 or greater)/(90 or less).

[8] The rubber composition according to any one of [1] to [7] described above, wherein the diene-based rubber further contains a natural rubber, and a mass ratio of the butadiene rubber to the natural rubber (butadiene rubber/natural rubber) is from 20/80 to 70/30.

[9] The rubber composition according to any one of [1] to [8] described above, wherein an amount of the modified polymer is 10 parts by mass or greater per 100 parts by mass of the diene-based rubber.

[10] The rubber composition according to any one of [1] to [9] described above, wherein an amount of the silica is from 8 to 130 parts by mass per 100 parts by mass of the diene-based rubber.

[11] A pneumatic tire comprising the rubber composition described in any one of [1] to [10] described above.

Advantageous Effects of Invention

As described below, according to the present invention, a modified polymer that significantly reduces heat build-up via the modification when the modified polymer is formed into a rubber composition, a rubber composition containing the modified polymer, and a pneumatic tire in which the rubber composition is used can be provided.

BRIEF DESCRIPTION OF DRAWINGS

FIG. 1 is a partial cross-sectional schematic view of a tire that illustrates an embodiment of a pneumatic tire of the present invention.

DESCRIPTION OF EMBODIMENT

A modified polymer, a rubber composition containing the modified polymer, and a pneumatic tire in which the rubber composition is used of the present invention will be described below.

Note that, in the present specification, a numerical range expressed by "(from) . . . to . . . " refers to a range including the numerical values written before and after "to" as the lower limit value and the upper limit value.

Modified Polymer

The modified polymer of the present invention is a modified polymer obtained by modifying a styrene-conjugated diene copolymer (A) by a nitrone compound (B). The content of styrene units in the styrene-conjugated diene copolymer (A) is 10% by mass or greater, and the proportion of vinyl bonds among all the double bonds contained in the styrene-conjugated diene copolymer (A) is 5 mol % or greater.

It is conceived that the heat build-up is significantly reduced due to the modification when the modified polymer of the present invention is formed into a rubber composition since the modified polymer has such a composition. Although the reason is not clear, it is assumed to be as follows.

In the modified polymer of the present invention, a styrene-conjugated diene copolymer having a specific structure is used as a polymer to be modified with the nitrone compound (B) as described above.

Specifically, a styrene-conjugated diene copolymer having the content of styrene units of 10% by mass or greater and the proportion of the vinyl bonds among all the double bonds of 5 mol % or greater is used. Note that the double bond derived from the vinyl bond has small steric hindrance and thus is easily modified with the nitrone compound (B). Furthermore, the styrene units contribute to enhancement of miscibility with the nitrone compound (B). It is conceived that, because of this, the modified polymer of the present invention has a structure in which the styrene-conjugated diene copolymer (A) is extremely uniformly modified with the nitrone compound (B). As a result, it is conceived that the effect of reducing the heat build-up due to the modification is exhibited efficiently and thus the heat build-up is significantly reduced due to the modification when the modified polymer of the present invention is formed into a rubber composition. This is also presumed from the fact that, as shown in comparative examples described below, when a styrene-conjugated diene copolymer that does not have the specific structure is used (Comparative Examples 1 and 2), reduction in heat build-up due to the modification is small.

It is conceived that, when the modified polymer of the present invention is a modified polymer in which a styrene-butadiene rubber is modified with a nitrone compound (B) (modified polymer produced by reacting a modifier having a nitrone group to a double bond contained in a styrene-butadiene rubber), the rubber composition having such a modified polymer, butadiene rubber, and silica exhibits high elongation at break and excellent low heat build-up.

It is conceived that, in a case where a nitrone compound (modifier) is introduced to a conjugated diene-based rubber (e.g. formulated system of a styrene-butadiene rubber and a butadiene rubber), since the interaction between the conjugated diene-based rubber after the modification (modified styrene-butadiene rubber and butadiene rubber) and the filler (e.g. silica) is increased, the low heat build-up of a compound containing these becomes excellent.

Furthermore, although a butadiene rubber typically exhibits poor uptake of fillers, when such a butadiene rubber is modified with a nitrone compound, the inventors of the present invention have found that the elongation at break tends to decrease due to increase in the pseudo-crosslinking points to the fillers of the butadiene rubber caused by the modification.

Because of this, by increasing the pseudo-crosslinking points to fillers of a styrene-butadiene rubber by modifying a styrene-butadiene rubber, which exhibits a relatively high uptake of fillers compared to that of a butadiene rubber, with a nitrone compound (B) (modifier) and by using this with a butadiene rubber, it is conceived that decrease in elongation at break is suppressed by suppressing the increase in pseudo-crosslinking points to fillers of the butadiene rubber, thereby achieving excellent low heat build-up at the same time.

The styrene-conjugated diene copolymer (A) and the nitrone compound (B) as well as the production method of the modified polymer of the present invention will be described in detail below.

Styrene-conjugated Diene Copolymer (A)

The styrene-conjugated diene copolymer (A) used in the modified polymer of the present invention is not particularly limited as long as the content of styrene units in the styrene-conjugated diene copolymer (A) is 10% by mass or greater, and the proportion of vinyl bonds among all the double bonds contained in the styrene-conjugated diene copolymer (A) is 5 mol % or greater.

The conjugated diene used during the production of the styrene-conjugated diene copolymer (A) is not particularly limited, and specific examples thereof include 1,3-butadiene, isoprene(2-methyl-1,3-butadiene), 2,3-dimethyl-1,3-butadiene, 2-chloro-1,3-butadiene, 1,3-pentadiene, and the like. Among these, 1,3-butadiene is preferable. That is, the styrene-conjugated diene copolymer (A) is preferably a styrene-butadiene rubber (SBR).

As described above, the content of the styrene units in the styrene-conjugated diene copolymer (A) (hereinafter, also referred to as "styrene unit content" or "styrene content") is 10% by mass or greater. In particular, the content is preferably 26% by mass or greater from the perspective of achieving greater enhancement of wet grip performance by the modification. Although the upper limit thereof is not particularly limited, the content is preferably 80% by mass or less, and more preferably 70% by mass or less.

The content of the styrene units (styrene content) in the styrene-conjugated diene copolymer (A) refers to the proportion (% by mass) of the styrene units relative to all the structural units constituting the styrene-conjugated diene copolymer (A).

In the present invention, microstructure of the styrene-conjugated diene copolymer (A) can be measured in accordance with JIS K 6239:2007 ("Rubber, raw, S-SBR Determination of the microstructure").

As described above, the proportion of vinyl bonds among all the double bonds contained in the styrene-conjugated diene copolymer (A) (hereinafter, also referred to as "vinyl bond content" or "vinyl content") is 5 mol % or greater. In particular, the proportion is preferably 10 mol % or greater, more preferably 20 mol % or greater, and even more preferably 35 mol % or greater, and from the perspective of further reducing the heat build-up by the modification, the proportion is particularly preferably 50 mol % or greater. Although the upper limit thereof is not particularly limited, the proportion is 100 mol % or less, and preferably 80 mol % or less.

Note that "proportion of vinyl bonds among all the double bonds contained in the styrene-conjugated diene copolymer (A)" refers to a proportion (mol %) of the vinyl bonds relative to all the double bonds derived from the conjugated diene contained in the styrene-conjugated diene copolymer (A). More specifically, it refers to the proportion (mol %) of 1,2-vinyl bonds among cis-1,4-bonds, trans-1,4-bonds, and 1,2-vinyl bonds, which are the bonding forms of the conjugated diene.

The proportion of 1,4-bonds among all the double bonds contained in the styrene-conjugated diene copolymer (A) is not particularly limited. From the perspective of making the proportion to be 95 mol % or less and achieving high elongation at break, excellent low heat build-up, and excellent strength characteristics, the proportion is preferably from 20 to 90 mol %, more preferably from 20 to 80 mol %, even more preferably form 25 to 65 mol %, and particularly preferably from 25 to 50 mol %, relative to the total amount of the double bonds.

The weight average molecular weight of the styrene-conjugated diene copolymer (A) is preferably from 100,000 to 1,500,000, more preferably from 100,000 to 1,400,000, and even more preferably from 300,000 to 1,300,000, from the perspective of handleability. The weight average molecular weight (Mw) of the styrene-conjugated diene copolymer (A) is measured by gel permeation chromatography (GPC) on the basis of standard polystyrene using tetrahydrofuran as a solvent.

Nitrone Compound (B)

The nitrone compound (B) used in the modified polymer of the present invention is not particularly limited as long as the nitrone compound (B) is a compound having a nitrone group represented by Formula (1) below.

[Chemical Formula 1]

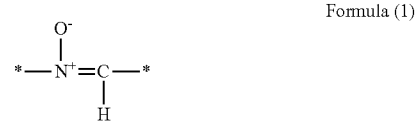

Formula (1)

In Formula (1), * indicates a bond position.

The number of nitrone groups contained in one molecule of the nitrone compound (B) is preferably from 1 to 3 groups.

The nitrone compound (B) is preferably a compound represented by Formula (2) below.

[Chemical Formula 2]

Formula (2)

In Formula (2) above, X and Y each independently represent an aliphatic hydrocarbon group, aromatic hydrocarbon group, or aromatic heterocycle group that may have a substituent.

Examples of the aliphatic hydrocarbon group represented by X or Y include alkyl groups, cycloalkyl groups, alkenyl groups, and the like.

Examples of the alkyl group include a methyl group, ethyl group, n-propyl group, isopropyl group, n-butyl group, isobutyl group, sec-butyl group, tert-butyl group, n-pentyl group, isopentyl group, neopentyl group, tert-pentyl group, 1-methylbutyl group, 2-methylbutyl group, 1,2-dimethylpropyl group, n-hexyl group, n-heptyl group, n-octyl group, and the like.

Among these, alkyl groups having from 1 to 18 carbons are preferable, and alkyl groups having from 1 to 6 carbons are more preferable.

Examples of the cycloalkyl group include a cyclopropyl group, cyclobutyl group, cyclopentyl group, cyclohexyl group, and the like.

Among these, cycloalkyl groups having from 3 to 10 carbons are preferable, and cycloalkyl groups having from 3 to 6 carbons are more preferable.

Examples of the alkenyl group include a vinyl group, 1-propenyl group, allyl group, isopropenyl group, 1-butenyl group, 2-butenyl group, and the like.

Among these, alkenyl groups having from 2 to 18 carbons are preferable, and alkenyl groups having from 2 to 6 carbons are more preferable.

Examples of the aromatic hydrocarbon group represented by X or Y include aryl groups, aralkyl groups, and the like.

Examples of the aryl group include a phenyl group, naphthyl group, anthryl group, phenanthryl group, biphenyl group, and the like. Among these, aryl groups having from 6 to 14 carbons are preferable, aryl groups having from 6 to 10 carbons are more preferable, and a phenyl group and naphthyl group are even more preferable.

Examples of the aralkyl group include a benzyl group, phenethyl group, phenylpropyl group, and the like. Among these, aralkyl groups having from 7 to 13 carbons are preferable, aralkyl groups having from 7 to 11 carbons are more preferable, and a benzyl group is even more preferable.

Examples of the aromatic heterocycle group represented by X or Y include a pyrrolyl group, furyl group, thienyl group, pyrazolyl group, imidazolyl group (imidazole group), oxazolyl group, isoxazolyl group, thiazolyl group, isothiazolyl group, pyridyl group (pyridine group), furan group, thiophene group, pyridazinyl group, pyrimidinyl group, piperazinyl group, and the like. Among these, a pyridyl group is preferable.

The substituent that may be contained in the group represented by X or Y is not particularly limited, and examples thereof include alkyl groups having from 1 to 4 carbons, hydroxy groups, amino groups, nitro groups, carboxy groups, sulfonyl groups, alkoxy groups, halogen atoms, and the like. Among these, carboxy groups are preferable. The substituent can be bonded to an aliphatic hydrocarbon group, aromatic hydrocarbon group, or aromatic heterocycle group directly or via an organic group. The organic group is not particularly limited.

Note that examples of the aromatic hydrocarbon group having such a substituent include aryl groups having an alkyl group, such as a tolyl group and xylyl group; aryl groups having a carboxy group, such as a carboxyphenyl group; aralkyl groups having a substituent, such as a methylbenzyl group, ethylbenzyl group, and methylphenethyl group; and the like.

The compound represented by Formula (2) above is preferably a compound represented by Formula (3) below.

The nitrone compound (B) is more preferably a compound having a carboxy group as a substituent.

The number of carboxy groups contained in one molecule of the nitrone compound (B) is preferably 1 group or greater, and can be set to 10 groups or less. The number of carboxy groups is more preferably from 1 to 4, and even more preferably from 1 to 2 groups.

Furthermore, the nitrone compound having a carboxy group is preferably a compound represented by Formula (3) below (carboxynitrone) from the perspectives of miscibility with a styrene-copolymer copolymerized rubber (e.g. styrene-butadiene rubber), excellent reactivity, high elongation at break, and excellent low heat build-up.

[Chemical Formula 3]

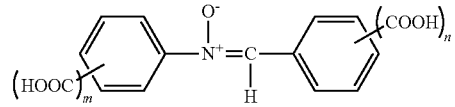

Formula (3)

In Formula (3), m and n each independently represent an integer of 0 to 5, and a sum of m and n is 1 or greater.

The integer represented by m is preferably an integer of 0 to 2, and more preferably an integer of 0 or 1, because solubility to a solvent during synthesis of the nitrone compound (B) will be better and thus synthesis will be easier.

The integer represented by n is preferably an integer of 0 to 2, and more preferably an integer of 0 or 1, because solubility to a solvent during synthesis of the nitrone compound (B) will be better and thus synthesis will be easier.

Furthermore, the sum of m and n (m+n) is preferably from 1 to 4, and more preferably 1 or 2.

The carboxynitrone represented by Formula (3) is not particularly limited; however, the carboxynitrone is preferably at least one type of compound selected from the group consisting of N-phenyl-α-(4-carboxyphenyl)nitrone represented by Formula (3-1) below, N-phenyl-α-(3-carboxyphenyl)nitrone represented by Formula (3-2) below, N-phenyl-α-(2-carboxyphenyl)nitrone represented by Formula (3-3) below, N-(4-carboxyphenyl)-α-phenylnitrone represented by Formula (3-4) below, N-(3-carboxyphenyl)-α-phenylnitrone represented by Formula (3-5) below, and N-(2-carboxyphenyl)-α-phenylnitrone represented by Formula (3-6) below.

[Chemical Formula 4]

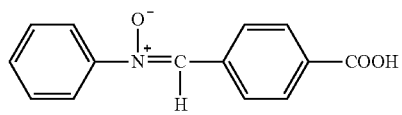

(3-1)

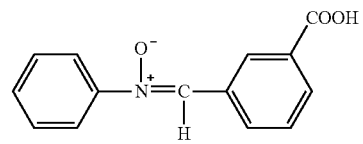

(3-2)

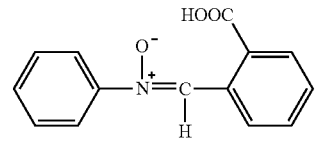

(3-3)

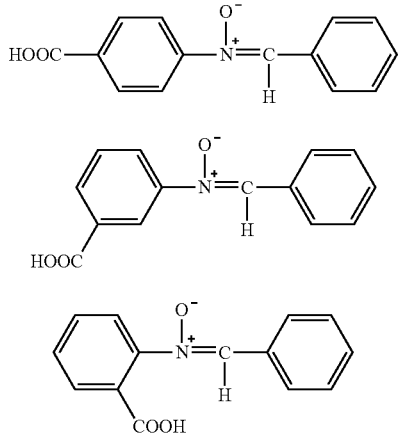

(3-4)

(3-5)

(3-6)

The method of synthesizing the nitrone compound (B) is not particularly limited, and a conventionally known method can be used. For example, nitrone having a nitrone group can be produced by stirring a compound having a hydroxyamino group (—NHOH) and a compound having an aldehyde group (—CHO) at a molar ratio of the hydroxyamino group to the aldehyde group (—NHOH/—CHO) of 1.0 to 1.5 in the presence of an organic solvent (e.g. methanol, ethanol, tetrahydrofuran, and the like) at room temperature for 1 to 24 hours to allow the both groups to react. When the nitrone compound (B) further has a carboxy group or the like, a compound having a hydroxyamino group and/or a compound having an aldehyde group needs to have a carboxy group or the like.

Method of Producing Modified Polymer

The method of producing the modified polymer of the present invention is not particularly limited, and examples of the method include a method in which the styrene-conjugated diene copolymer (A) and the nitrone compound (B) described above are mixed at 100 to 200° C. for 1 to 30 minutes.

At this time, as shown in Formula (4) below or Formula (5) below, a cycloaddition reaction occurs between a double bond derived from the conjugated diene contained in the styrene-conjugated diene copolymer (A) and a nitrone group contained in the nitrone compound (B) to form a five-membered ring. Note that Formula (4) below represents a reaction between a 1,4-bond and a nitrone compound, and Formula (5) below represents a reaction between a 1,2-vinyl bond and a nitrone compound.

[Chemical Formula 5]

Formula (4)

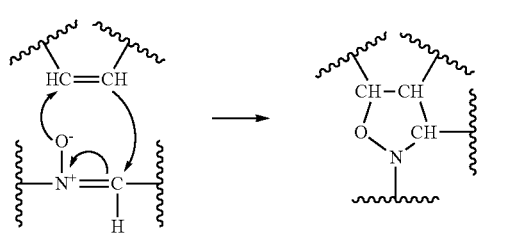

[Chemical Formula 6]

Formula (5)

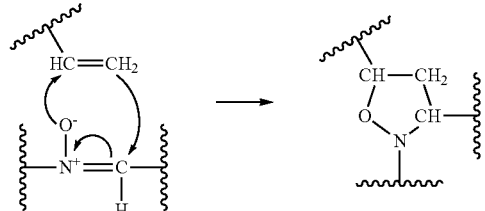

The amount of the nitrone compound (B) to be reacted with the styrene-conjugated diene copolymer (A) is preferably from 0.1 to 10 parts by mass, and more preferably from 0.3 to 5 parts by mass, per 100 parts by mass of the styrene-conjugated diene copolymer (A).

Furthermore, the amount of the nitrone compound (B) to be used during the production of the modified polymer can be set to 0.01 to 2.0 mol %, and preferably from 0.02 to 1.5 mol %, of the double bonds contained in the styrene-conjugated diene copolymer (A) (e.g. styrene-butadiene rubber) from the perspectives of achieving high elongation at break, excellent low heat build-up, and excellent handleability.

The modification ratio of the modified polymer of the present invention is not particularly limited; however, the modification ratio is preferably 0.10 mol % or greater, and from the perspectives of further reducing heat build-up by the modification, the modification ratio is more preferably 0.20 mol % or greater. Although the upper limit of the modification ratio is not particularly limited, the modification ratio is preferably 3.0 mol % or less, and more preferably 2.0 mol % or less.

Note that "modification ratio" represents the percentage (mol %) of bonds modified with the nitrone compound (B) among all the double bonds derived from the conjugated diene contained in the styrene-conjugated diene copolymer (A), and more specifically refers to the percentage (mol %) of structures of Formula (4) above or Formula (5) above formed due to the modification caused by the nitrone compound (B). The modification ratio can be determined by NMR analysis of the styrene-conjugated diene copolymer (A) and the modified polymer (that is, the polymers before and after the modification).

Rubber Composition

The rubber composition of the present invention (hereinafter, also referred to as "composition of the present invention") is a rubber composition containing the modified polymer of the present invention.

The modified polymer of the present invention is as described above. A single type or a combination of two or more types of modified polymers can be used as the modified polymer.

When the composition of the present invention contains a diene-based rubber except the modified polymer (hereinafter, "diene-based rubber except the modified polymer" is also simply referred to as "diene-based rubber"), the content of the modified polymer relative to the total amount of the diene-based rubber except the modified polymer and the modified polymer of the present invention is not particularly limited; however, the content is preferably from 10 to 100% by mass, can be set to less than 100% by mass, and is more preferably from 10 to 60% by mass. Note that when the content of the modified polymer is 100% by mass, the composition of the present invention does not contain the diene-based rubber except the modified polymer (hereinafter, "diene-based rubber except the modified polymer" is also simply referred to as "diene-based rubber").

The composition of the present invention may further contain another component besides the modified polymer of the present invention in a range that does not impair the effect and the object of the present invention. Examples of such a component include diene-based rubbers except the modified polymer of the present invention; and various additives that are typically used in rubber compositions, such as silica, carbon black, silane coupling agents (e.g. Si 69 manufactured by Evonik Degussa and Si 363 manufactured by Evonik Degussa), zinc oxide (zinc white), stearic acid, anti-aging agents, processing aids, oils, liquid polymers, waxes, terpene resins, thermosetting resins, vulcanizing agents (e.g. sulfur), and vulcanization accelerators.

Diene-based Rubber

The composition of the present invention preferably further contains a diene-based rubber except the modified polymer described above.

Such a diene-based rubber is not particularly limited, and specific examples thereof include natural rubber (NR), isoprene rubber (IR), butadiene rubber (BR), aromatic vinyl-conjugated diene copolymer rubber, acrylonitrile-butadiene copolymer rubber (NBR), butyl rubber (IIR), halogenated butyl rubber (Br-IIR, Cl-IIR), chloroprene rubber (CR), and the like. For the diene-based rubber (A), a single type of the diene-based rubbers may be used alone, or two or more types of the diene-based rubbers may be used in combination.

The diene-based rubber except the modified polymer is preferably at least one type selected from the group consisting of butadiene rubbers, aromatic vinyl-conjugated diene copolymers, and natural rubbers.

In the rubber composition of the present invention, an example of preferable aspects is one in which the modified polymer and the butadiene rubber are contained.

Furthermore, another example of preferable aspects of the rubber composition of the present invention is one in which the modified polymer, the butadiene rubber, and the aromatic vinyl-conjugated diene copolymer and/or natural rubber are contained.

Butadiene Rubber

The butadiene rubber will be described below. The butadiene rubber that can be further contained as the diene-based rubber except the modified polymer in the rubber composition of the present invention is not particularly limited. Examples thereof include conventionally known butadiene rubbers.

The weight average molecular weight of the butadiene rubber is preferably from 100,000 to 1,000,000, and more preferably from 300,000 to 800,000, from the perspective of handleability. The weight average molecular weight (Mw) of the butadiene rubber is measured by gel permeation chromatography (GPC) on the basis of standard polystyrene using tetrahydrofuran as a solvent.

The production of the butadiene rubber is not particularly limited. Examples thereof include conventionally known production methods. A single type of the butadiene rubbers may be used alone, or two or more types may be used in combination.

Note that an example of a preferable aspect is one in which the butadiene rubber is not modified with the nitrone compound (B) described above.

In the present invention, the mass ratio of the modified polymer to the butadiene rubber (modified polymer/butadiene rubber) is preferably from 95/5 to 68/32, and more preferably from 90/10 to 70/30, from the perspective of achieving high elongation at break, excellent low heat build-up, and excellent handleability.

Natural Rubber

The natural rubber will be described below. The natural rubber that can be further contained as the diene-based rubber except the modified polymer in the rubber composition of the present invention is not particularly limited. Examples thereof include conventionally known natural rubbers.

The mass ratio of the butadiene rubber to the natural rubber (butadiene rubber/natural rubber) is preferably from 20/80 to 70/30, and more preferably from 20/80 to 60/40, from the perspective of achieving high elongation at break, excellent low heat build-up, and excellent handleability.

Aromatic Vinyl-conjugated Diene Copolymer Rubber

The aromatic vinyl-conjugated diene copolymer rubber will be described below. The aromatic vinyl-conjugated diene copolymer rubber that can be further contained as the diene-based rubber except the modified polymer in the rubber composition of the present invention is not particularly limited.

In the present invention, from the perspective of wear resistance of the resulting tire, the aromatic vinyl-conjugated diene copolymer rubber is preferably used as the diene-based rubber, and a combined use of the aromatic vinyl-conjugated diene copolymer and the butadiene rubber (BR) is more preferable.

Furthermore, examples of the aromatic vinyl-conjugated diene copolymer rubber include styrene-butadiene copolymer rubbers (styrene-butadiene rubber, SBR), styrene-isoprene copolymer rubbers, and the like. Among these, the styrene-butadiene copolymer rubber (SBR) is preferable from the perspective of achieving excellent wear resistance of a resulting tire, high elongation at break, and excellent low heat build-up. The styrene-butadiene rubber may be the same styrene-butadiene rubber as that used during the production of the modified polymer for example.

The content of the aromatic vinyl units in the aromatic vinyl-conjugated diene copolymer is preferably from 20 to 80% by mass, and more preferably from 26 to 70% by mass, from the perspective of the balance between wear resistance and toughness of a resulting tire.

Furthermore, the proportion of the vinyl bonds among all the double bonds contained in the aromatic vinyl-conjugated diene copolymer is preferably from 20 to 80 mol %, and more preferably from 25 to 65 mol %. Note that "proportion of the vinyl bonds" refers to the proportion (mol %) of the vinyl bonds among all the double bonds derived from the conjugated diene contained in the aromatic vinyl-conjugated diene copolymer. More specifically, it refers to the proportion of 1,2-vinyl bonds among cis-1,4-bonds, trans-1,4-bonds, and 1,2-vinyl bonds, which are the bonding forms of the conjugated diene.

The weight average molecular weight of the aromatic vinyl-conjugated diene copolymer is preferably from 100,000 to 1,500,000, more preferably from 100,000 to 1,400,000, and even more preferably from 600,000 to 1,300,000, from the perspective of the balance between processability and toughness of a resulting tire. The method of measuring weight average molecular weight is the same as that for the styrene-conjugated diene copolymer (A) described above.

The method of producing the aromatic vinyl-conjugated diene copolymer is not particularly limited and can be produced by a conventionally known method.

Furthermore, aromatic vinyl and conjugated diene as monomers used during the production of the aromatic vinyl-conjugated diene copolymer are not particularly limited.

Specific examples of the conjugated diene monomer include the same monomers exemplified for the styrene-conjugated diene copolymer (A) described above.

Examples of the aromatic vinyl monomer include styrene, 2-methylstyrene, 3-methylstyrene, 4-methylstyrene, α-methylstyrene, 2,4-dimethylstyrene, 2,4-diisopropylstyrene, 4-tert-butylstyrene, divinylbenzene, tert-butoxystyrene, vinylbenzyldimethylamine, (4-vinylbenzyl)dimethylaminoethyl ether, N,N-dimethyl aminoethylstyrene, vinyl pyridine, and the like.

In the present invention, the content of the aromatic vinyl-conjugated diene copolymer when it is used is not particularly limited; however, from the perspective of wear resistance of a resulting tire, the content is preferably from 0 to 90% by mass, and more preferably from 40 to 90% by mass, relative to the total amount of the diene-based rubber and the modified polymer described above.

Furthermore, when the butadiene rubber (BR) described above is used together with the aromatic vinyl-conjugated diene copolymer, the content of the butadiene rubber (BR) is not particularly limited; however, the content is preferably from 10 to 50% by mass, and more preferably from 20 to 40% by mass, relative to the total amount of the diene-based rubber and the modified polymer described above.

In the present invention, the mass ratio of the modified polymer to the aromatic vinyl-conjugated diene copolymer (modified polymer/aromatic vinyl-conjugated diene copolymer) is preferably from 100/0 to 10/90, and more preferably from 100/0 to 40/60, from the perspective of achieving high elongation at break, excellent low heat build-up, and excellent handleability.

Furthermore, from the same reasons as described above, the mass ratio of the modified polymer to the aromatic vinyl-conjugated diene copolymer (modified polymer/aromatic vinyl-conjugated diene copolymer) is preferably (10 or greater)/(90 or less) (in this case, the mass ratio described above becomes (10/90) or greater, and more preferably (40 or greater)/(60 or less) (in this case, the mass ratio described above becomes (40/60) or greater). The upper limit of the mass ratio can be set to less than 100.

When the rubber composition of the present invention contains the modified polymer and at least one type selected from the group consisting of butadiene rubber, natural rubber, and aromatic vinyl-conjugated diene copolymer rubber, the amount of the modified polymer is preferably 10 parts by mass or greater, more preferably from 30 to 80 parts by mass, and even more preferably from 50 to 80 parts by mass, per 100 parts by mass total of the modified polymer and the diene-based rubber except the modified polymer from the perspectives of achieving high elongation at break, excellent low heat build-up, and excellent handleability.

Furthermore, when the rubber composition of the present invention contains the modified polymer, butadiene rubber, and natural rubber and/or aromatic vinyl-conjugated diene copolymer rubber, the amount of the modified polymer is preferably 10 parts by mass or greater, more preferably from 30 to 80 parts by mass, and even more preferably from 50 to 80 parts by mass, per 100 parts by mass total of the modified polymer and the diene-based rubber except the modified polymer from the perspectives of achieving high elongation at break, excellent low heat build-up, and excellent handleability.

The amount of the nitrone compound (B) introduced to the modified polymer is preferably from 0.1 to 10 parts by mass, and more preferably from 0.1 to 5.0 parts by mass, per 100 parts by mass total of the modified polymer and the diene-based rubber except the modified polymer from the perspectives of achieving high elongation at break, excellent low heat build-up, and excellent handleability.

A single type or a combination of two or more types of modified polymers can be used as the modified polymer.

Silica

The composition of the present invention preferably further contains silica.

The silica is not particularly limited, and any conventionally known silica that is compounded in a rubber composition for use in tires or the like can be used.

Specific examples of the silica include wet silica, dry silica, fumed silica, diatomaceous earth, and the like. For the silica, a single type of the silicas may be used alone, or two or more types of the silicas may be used in combination.

In the present invention, the silica is preferably wet silica from the perspective of reinforcing property of rubber.

The content of the silica is not particularly limited; however, the content is preferably from 8 to 130 parts by mass, more preferably from 20 to 100 parts by mass, and even more preferably from 25 to 95 parts by mass, per 100 parts by mass total of the modified polymer and the diene-based rubber (diene-based rubber except the modified polymer) (note that, when the composition of the present invention does not contain the diene-based rubber except the modified polymer, the "100 parts by mass" described above, which is a reference, refers to "100 parts by mass of the modified polymer"; hereinafter the same).

Carbon Black

The composition of the present invention preferably further contains carbon black.

The carbon black is not particularly limited and, for example, carbon blacks with various grades, such as SAF-HS, SAF, ISAF-HS, ISAF, ISAF-LS, IISAF-HS, HAF-HS, HAF, HAF-LS, and FEF, can be used.

The content of the carbon black is not particularly limited; however, the content is preferably from 1 to 100 parts by mass, and more preferably form 3 to 60 parts by mass, per 100 parts by mass total of the modified polymer and the diene-based rubber.

Method of Producing Rubber Composition

The method for producing the composition of the present invention is not particularly limited, and specific examples thereof include a method whereby each of the above-mentioned components is kneaded using a publicly known method and device (e.g. Banbury mixer, kneader, roll, and the like). When the composition of the present invention contains sulfur or a vulcanization accelerator, it is preferable to mix the other components, excluding the sulfur and the vulcanization accelerator, first (e.g. mixing at 60 to 160° C.), cool, and then further blend the sulfur or the vulcanization accelerator.

In addition, the composition of the present invention can be vulcanized or crosslinked under conventional, publicly known vulcanizing or crosslinking conditions.

Pneumatic Tire

The pneumatic tire of the present invention is a pneumatic tire in which the composition of the present invention described above is used. In particular, the pneumatic tire is preferably a pneumatic tire in which the composition of the present invention is used in the tire tread.

FIG. 1 is a partial cross-sectional schematic view of a tire that represents one embodiment of the pneumatic tire of the present invention, but the pneumatic tire of the present invention is not limited to the embodiment illustrated in FIG. 1.

In FIG. 1, reference number 1 denotes a bead portion, reference number 2 denotes a sidewall portion, and reference number 3 denotes a tire tread portion.

In addition, a carcass layer 4, in which a fiber cord is embedded, is mounted between a left-right pair of bead portions 1, and ends of the carcass layer 4 are wound by being folded around bead cores 5 and a bead filler 6 from an inner side to an outer side of the tire.

In the tire tread portion 3, a belt layer 7 is provided along the entire periphery of the tire on the outer side of the carcass layer 4.

Additionally, rim cushions 8 are provided in parts of the bead portions 1 that are in contact with a rim.

The pneumatic tire of the present invention can be produced, for example, in accordance with conventionally known methods. In addition to ordinary air or air with an adjusted oxygen partial pressure, inert gasses such as nitrogen, argon, and helium can be used as the gas with which the tire is filled.

EXAMPLES

Hereinafter, the present invention will be further described in detail using working examples; however, the present invention is not limited thereto.
Working Examples 1 to 11 and Comparative Examples 1 and 2 shown in Table 1
Synthesis of Nitrone Compound (Compound 1)

In a 2 L egg-plant shaped flask, methanol heated to 40° C. (900 mL) was placed, and then terephthalaldehydic acid represented by Formula (b-1) below (30.0 g) was added thereto and dissolved. In this solution, a solution in which phenylhydroxylamine represented by Formula (a-1) below (21.8 g) was dissolved in methanol (100 mL) was added and stirred at room temperature for 19 hours. After the completion of stirring, a nitrone compound represented by Formula (c-1) below (41.7 g; carboxynitrone, N-phenyl-α-(4-carboxyphenyl)nitrone), mp: 243° C., molecular weight: 241) was obtained by recrystallization from methanol. The yield was 86%. The obtained nitrone compound was used as the compound 1.

Chemical Formula 7

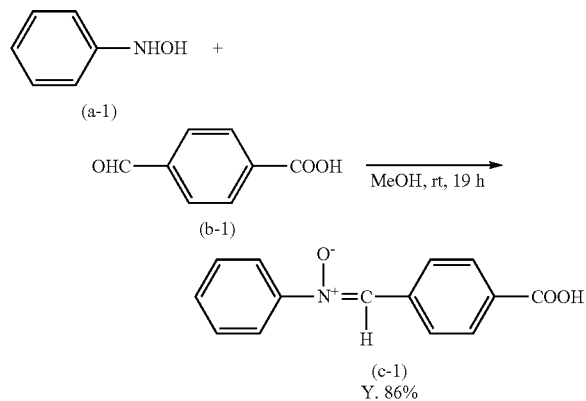

Synthesis of Nitrone Compound (Compound 2)

In a 2 L egg-plant shaped flask, methanol heated to 40° C. (900 mL) was placed, and then 2-pyridinecarboxaldehyde represented by Formula (b-2) below (21.4 g) was added thereto and dissolved. In this solution, a solution in which phenylhydroxylamine represented by Formula (a-2) below (21.8 g) was dissolved in methanol (100 mL) was added and stirred at room temperature for 19 hours. After the completion of stirring, a nitrone compound (39.0 g; pyridylnitrone) represented by Formula (c-2) below was obtained by recrystallization from methanol. The yield was 90%. The obtained nitrone compound was used as the compound 2.

Chemical Formula 8

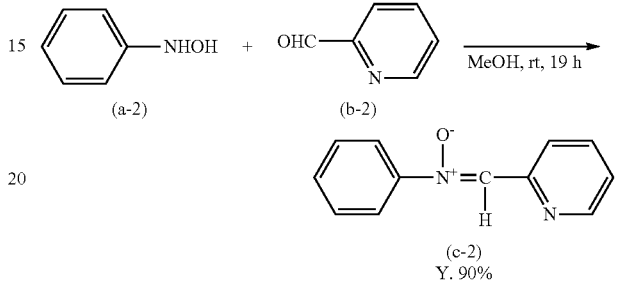

Synthesis of Nitrone Compound (Compound 3)

In a 300 mL egg-plant shaped flask, imidazole-4-carboxyaldehyde represented by Formula (b-3) below (35 g) and ethanol (10 mL) were placed, and then a solution in which phenylhydroxylamine represented by Formula (a-3) below (43.65 g) was dissolved in ethanol (70 mL) was added and stirred at room temperature for 22 hours. After the completion of stirring, a nitrone compound (imidazole nitrone) represented by Formula (c-3) below was obtained by recrystallization from ethanol. The obtained nitrone compound was used as the compound 3.

Chemical Formula 9

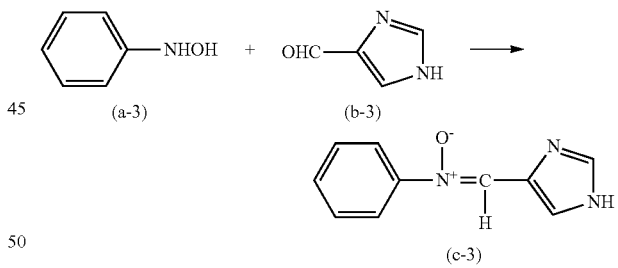

Production of Modified Polymer

Modified polymers in which SBR is modified with a nitrone compound (B) (modified polymers of working examples and comparative examples) were obtained by mixing SBR having "styrene unit content of SBR before modification" and "vinyl bond content of SBR before modification" described in Table 1 (100 parts by mass (in the case of an oil extended product, 100 parts by mass of net amount of SBR)) and a nitrone compound described in Table 1 (compounds 1 to 3 synthesized as described above) (1 part by mass; only for Working Example 8, 7 parts by mass; and only for Working Example 9, 0.5 parts by mass) using a mixer (160° C.) for 5 minutes.

Styrene Unit Content

Herein, the styrene unit content refers to "content of styrene units in a styrene-conjugated diene copolymer" described above.

Vinyl Bond Content

The vinyl bond content refers to "proportion of vinyl bonds among all the double bonds contained in a styrene-conjugated diene copolymer" described above.

Modification Ratio

Furthermore, NMR analysis of the obtained modified polymer was performed to determine the modification ratio. Specifically, in the case of an example where the compound 1 (modifier 1 described below) was used as the nitrone compound (B), the peak area around 8.08 ppm (assigned to two protons adjacent to a carboxy group) was measured by $^1$H-NMR analysis using $CDCl_3$ as a solvent ($CDCl_3$, 400 MHz, TMS) for the polymers before and after the modification, thereby calculating the modification ratio.

Furthermore, also for the examples where the compounds 2 and 3 and modifier 2 described below were used as the nitrone compound (B), the modification ratio was calculated for each case in the same manner except for measuring the peak area derived from pyridyl groups or imidazolyl groups.

Note that $^1$H-NMR analysis for the polymer after the modification (modified polymer) was performed by using a sample prepared by dissolving the modified product in toluene, repeating purification twice in which the obtained product was precipitated in methanol, and then drying under reduced pressure. The results are shown in the tables.

Note that the details of SBR used in the production of the modified polymers in Working Examples 1 to 11 described in Table 1 were as described below.

Working Example 1: Tufdene 1000 (manufactured by Asahi Kasei Chemicals Corporation)

Working Example 2: Tufdene 2000R (manufactured by Asahi Kasei Chemicals Corporation)

Working Example 3: Nipol 1502 (manufactured by Zeon Corporation)

Working Example 4: Nipol NS460 (manufactured by Zeon Corporation; oil extended product (amount of oil extension: 37.5% by mass))

Working Example 5: Nipol 9548 (manufactured by Zeon Corporation; oil extended product (amount of oil extension: 37.5% by mass))

Working Example 6: Tufdene 3835 (manufactured by Asahi Kasei Chemicals Corporation; oil extended product (amount of oil extension: 37.5% by mass))

Working Example 7: Nipol NS522 (manufactured by Zeon Corporation)

Working Example 8: Nipol NS460 (manufactured by Zeon Corporation; oil extended product (amount of oil extension: 37.5% by mass))

Working Example 9: Tufdene 1000 (manufactured by Asahi Kasei Chemicals Corporation)

Working Example 10: Tufdene 3835 (manufactured by Asahi Kasei Chemicals Corporation; oil extended product (amount of oil extension: 37.5% by mass))

Working Example 11: Tufdene 3835 (manufactured by Asahi Kasei Chemicals Corporation; oil extended product (amount of oil extension: 37.5% by mass))

Preparation of Rubber Composition

The components described in the rows of rubber composition in Table 1 below were blended at the proportions (part by mass) described in the same table. Specifically, a mixture was obtained by mixing the components described in Table 1 below, excluding the sulfur and the vulcanization accelerator, for 5 minutes in a Banbury mixer at 80° C. Thereafter, a roll was used to mix the sulfur and the vulcanization accelerator to the mixture to obtain a rubber composition.

Production of Vulcanized Rubber Sheet for Evaluation

A vulcanized rubber sheet for evaluation was produced by press-vulcanizing the rubber composition (unvulcanized) prepared as described above for 20 minutes at 160° C. in a mold (15 cm×15 cm×0.2 cm).

tan δ (0° C.)

The loss tangent at a temperature of 0° C., tan δ (0° C.), was measured for the vulcanized rubber sheet for evaluation produced as described above using a viscoelastic spectrometer (manufactured by Toyo Seiki Seisaku-sho, Ltd.) under the following conditions: 10% initial distortion, ±2% amplitude, and 20 Hz frequency.

The results are shown in Table 1. Note that the results are shown in percentage taking the value for the case where each of the SBRs prior to the modification (30 parts by mass) was used in place of each of the modified polymers (30 parts by mass) as 100%.

A larger value of tan δ (0° C.) indicates superior wet grip performance.

tan δ (60° C.)

The loss tangent at a temperature of 60° C., tan δ (60° C.), was measured for the vulcanized rubber sheet produced as described above using a viscoelastic spectrometer (manufactured by Toyo Seiki Seisaku-sho, Ltd.) under the following conditions: 10% initial distortion, ±2% amplitude, and 20 Hz frequency.

The results are shown in Table 1. Note that the results are shown in percentage taking the value for the case where each of the SBRs prior to the modification (30 parts by mass) was used in place of each of the modified polymers (30 parts by mass) as 100%.

A smaller value of tan δ (60° C.) indicates lower heat build-up, and thus is preferable.

TABLE 1

| | | Comparative Example 1 | Comparative Example 2 | Working Example 1 | Working Example 2 | Working Example 3 | Working Example 4 | Working Example 5 | Working Example 6 | Working Example 7 | Working Example 8 | Working Example 9 | Working Example 10 | Working Example 11 |
|---|---|---|---|---|---|---|---|---|---|---|---|---|---|---|
| Modified Polymer | Styrene unit content of SBR before modification (mass %) | 7.0 | 15 | 18 | 25 | 25 | 27 | 35 | 35 | 40 | 27 | 18 | 35 | 35 |
| | Vinyl bond content of SBR before modification (mass %) | 16 | 4.2 | 11 | 10 | 15 | 69 | 15 | 45 | 41 | 69 | 11 | 45 | 45 |
| | Nitrone compound | Compound 1 | Compound 1 | Compound 1 | Compound 1 | Compound 1 | Compound 1 | Compound 1 | Compound 1 | Compound 1 | Compound 1 | Compound 1 | Compound 2 | Compound 3 |
| | Modification ratio (mol %) | 0.12 | 0.11 | 0.22 | 0.26 | 0.26 | 0.31 | 0.30 | 0.28 | 0.32 | 2.00 | 0.11 | 0.29 | 0.27 |
| Rubber Composition | BR | 30.00 | 30.00 | 30.00 | 30.00 | 30.00 | 30.00 | 30.00 | 30.00 | 30.00 | 30.00 | 30.00 | 30.00 | 30.00 |
| | SBR | 40.00 | 40.00 | 40.00 | 40.00 | 40.00 | 40.00 | 40.00 | 40.00 | 40.00 | 40.00 | 40.00 | 40.00 | 40.00 |
| | Modified Polymer | 30 | 30 | 30 | 30 | 30 | 30 | 30 | 30 | 30 | 30 | 30 | 30 | 30 |
| | Silica | 70.00 | 70.00 | 70.00 | 70.00 | 70.00 | 70.00 | 70.00 | 70.00 | 70.00 | 70.00 | 70.00 | 70.00 | 70.00 |
| | Carbon black | 5.00 | 5.00 | 5.00 | 5.00 | 5.00 | 5.00 | 5.00 | 5.00 | 5.00 | 5.00 | 5.00 | 5.00 | 5.00 |
| | Zinc oxide | 3.00 | 3.00 | 3.00 | 3.00 | 3.00 | 3.00 | 3.00 | 3.00 | 3.00 | 3.00 | 3.00 | 3.00 | 3.00 |
| | Stearic acid | 2.00 | 2.00 | 2.00 | 2.00 | 2.00 | 2.00 | 2.00 | 2.00 | 2.00 | 2.00 | 2.00 | 2.00 | 2.00 |
| | Anti-aging agent | 1.50 | 1.50 | 1.50 | 1.50 | 1.50 | 1.50 | 1.50 | 1.50 | 1.50 | 1.50 | 1.50 | 1.50 | 1.50 |
| | Silane coupling agent | 5.60 | 5.60 | 5.60 | 5.60 | 5.60 | 5.60 | 5.60 | 5.60 | 5.60 | 5.60 | 5.60 | 5.60 | 5.60 |
| | Process oil | 10.00 | 10.00 | 10.00 | 10.00 | 10.00 | 10.00 | 10.00 | 10.00 | 10.00 | 10.00 | 10.00 | 10.00 | 10.00 |
| | Sulfur | 1.50 | 1.50 | 1.50 | 1.50 | 1.50 | 1.50 | 1.50 | 1.50 | 1.50 | 1.50 | 1.50 | 1.50 | 1.50 |
| | Vulcanization accelerator (CZ) | 1.70 | 1.70 | 1.70 | 1.70 | 1.70 | 1.70 | 1.70 | 1.70 | 1.70 | 1.70 | 1.70 | 1.70 | 1.70 |
| | Vulcanization accelerator (DPG) | 2.00 | 2.00 | 2.00 | 2.00 | 2.00 | 2.00 | 2.00 | 2.00 | 2.00 | 2.00 | 2.00 | 2.00 | 2.00 |
| | tan δ (0° C.) | 99% | 100% | 98% | 94% | 97% | 103% | 101% | 103% | 102% | 102% | 99% | 105% | 108% |
| | tan δ (60° C.) | 95% | 96% | 87% | 86% | 84% | 81% | 82% | 84% | 86% | 81% | 90% | 90% | 86% |

The details of each component of the rubber compositions shown in Table 1 above are as follows.

BR: Butadiene rubber (Nipol BR 1220, manufactured by Zeon Corporation)

SBR: Styrene-butadiene rubber (E580, manufactured by Asahi Kasei Chemicals Corporation; oil extended product (amount of oil extension: 37.5% by mass))

Modified polymer: each of the modified polymers synthesized as described above (modified polymers of each of working examples and comparative examples)

Silica: Zeosil 165GR (manufactured by Rhodia Silica Korea Co., Ltd.)

Carbon black: Show Black N339 (manufactured by Cabot Japan)

Zinc oxide: Zinc White No. 3 (manufactured by Seido Chemical Industry Co., Ltd.)

Stearic acid: Stearic acid YR (manufactured by NOF Corporation)

Anti-aging agent: SANTOFLEX 6PPD (manufactured by Soltia Europe)

Silane coupling agent: Si 69 (manufactured by Evonik Degussa)

Process oil: Extract No. 4S (manufactured by Showa Shell Sekiyu K.K.)

Sulfur: oil-treated sulfur (manufactured by Karuizawa Refinery Ltd.)

Vulcanization accelerator (CZ): Nocceler CZ-G (manufactured by Ouchi Shinko Chemical Industrial Co., Ltd.)

Vulcanization accelerator (DPG): Soxinol D-G (manufactured by Sumitomo Chemical Co., Ltd.)

Regarding Working Examples 1 to 11 in Table 1

As is clear from Table 1, in all of Working Examples 1 to 11 in which the styrene-conjugated diene copolymer having a specific structure (styrene unit content and proportion of vinyl bonds) was used as the polymer to be modified, heat build-up was significantly reduced due to the modification.

When Working Examples 1 to 9 were compared, Working Examples 1 to 8 in which the modification ratio of the modified polymer was 0.20 mol % or greater resulted in even greater reduction in heat build-up due to the modification.

When Working Examples 1 to 8 were compared, Working Examples 4 to 8 in which the styrene unit content was 26% by mass or greater resulted in greater enhancement in wet grip performance due to the modification. Among these, Working Examples 4 and 8 in which the proportion of the vinyl bond was 50 mol % or greater resulted in even greater reduction in heat build-up due to the modification.

When Working Examples 6, 10, and 11 were compared, Working Example 6 in which a compound represented by Formula (3) above (carboxynitrone) was used as the nitrone compound (B) resulted in even greater reduction in heat build-up due to the modification.

On the other hand, in both of Comparative Examples 1 and 2 in which a styrene-conjugated diene copolymer other than the styrene-conjugated diene copolymer having the specific structure was used as the polymer to be modified, reduction in heat build-up due to the modification was small.

Working Examples 1 to 11 and Standard Examples 1 and 2 shown in Tables 2 and 3

Synthesis of Modifier 1 as Nitrone Compound (B)

A nitrone compound was synthesized in the same manner as in the synthesis of the nitrone compound (compound 1) described above. The obtained nitrone compound was used as the modifier 1 hereinafter.

Synthesis of Modifier 2 as Nitrone Compound (B)

In a mixed solvent of 200 mL of water and 200 mL of ethanol, 38.513 g (0.72 mol) of ammonium chloride was dissolved, and then 123.11 g (1 mol) of nitrobenzene was added thereto. Thereafter, zinc was gradually added to a 1% hydrochloric acid aqueous solution, and substitution was performed 2 or 3 times using water. In an ice bath, the zinc was gradually added to the mixture while the mixture is being cooled. Thereafter, the mixture was kept in the ice bath and stirred for 12 hours. After the zinc was filtered, 107.1 g (1 mol) of p-pyridylaldehyde was gradually added to the filtrate in the ice bath, and the mixture was further stirred for 12 hours. After the completion of the reaction, water and ethanol were removed by distillation under reduced pressure, and then 4-pyridyl-N-phenylnitrone (pale yellow solid powder) was obtained by recrystallizing from ethanol. The obtained 4-pyridyl-N-phenylnitrone was used as the modifier 2.

Production of Modified Polymer

A modified polymer in which a raw material styrene-butadiene rubber was modified with the modifier described above (modified SBRs 1 to 5 and P modified polymer) was produced by mixing a raw material styrene-butadiene rubber 1 or raw material styrene-butadiene rubber 2 in the row of the modified polymer production in each of the tables below and the modifier 1 or modifier 2 synthesized as described above at amounts described in the same table (part by mass) using a mixer at 160° C. for 5 minutes.

The raw material styrene-butadiene rubber 1 in the row of the modified polymer production in Table 2 was Nipol NS522, manufactured by Zeon Corporation (solution polymerized styrene-butadiene rubber; weight average molecular weight: 1,360,000; styrene content: 40% by mass; vinyl (1,2 unit) content: 41 mol %; 1,4 unit content: 59 mol %; amount of oil extension: 37.5% by mass).

The raw material styrene-butadiene rubber 2 in the row of the modified polymer production in Table 3 was E580, manufactured by Asahi Kasei Chemicals Corporation (solution polymerized styrene-butadiene rubber; weight average molecular weight: 800,000; styrene content: 37% by mass; vinyl (1,2 unit) content: 45 mol %; amount of oil extension: 37.5% by mass).

Modification Ratio

NMR analysis of each of the modified polymers obtained as described above was performed in the same manner to determine the modification ratio. The results are shown in the tables.

Production of Rubber Composition

The components described in the rows of rubber composition in the tables below were blended at the proportions (part by mass) described in the same tables. Specifically, a mixture was obtained by mixing the components described in the tables below, excluding the sulfur and the vulcanization accelerator, for 5 minutes in a Banbury mixer at 120° C. Thereafter, a roll was used to mix the sulfur and the vulcanization accelerator to the mixture to obtain a rubber composition.

Note that, when the rubber used in the production of the rubber composition was an oil-extended rubber, the amount of the rubber was described in two lines in the tables below. The value in the upper line indicates the amount of the oil extended product, and the value in the lower line indicates the net amount of the rubber.

Furthermore, in Tables 2 and 3, the diene-based rubber of "amount of modifier introduced to modified polymer in 100 parts by mass of diene-based rubber" indicates the modified polymer and the other diene-based rubber except the modified polymer.

Production of Vulcanized Rubber Sheet for Evaluation

A vulcanized rubber sheet for evaluation was produced by press-vulcanizing the rubber composition (unvulcanized) produced as described above for 20 minutes at 160° C. in a mold (15 cm×15 cm×0.2 cm).

Evaluation

The following evaluations were performed using the vulcanized rubber sheets for evaluation produced as described above. The results are shown in the tables. Each result of the evaluations is indicated by an index which takes the value of the Standard Example 1 or Standard Example 2 in each table as 100.

Heat Build-up

The loss tangent at a temperature of 60° C., tan δ (60° C.), was measured for the vulcanized rubber sheet for evaluation produced as described above using a viscoelastic spectrometer (manufactured by Toyo Seiki Seisaku-sho, Ltd.) under the following conditions: 10% initial distortion, ±2% amplitude, and 20 Hz frequency. A smaller index value of tan δ (60° C.) indicates lower heat build-up and lower friction, and thus is preferable.

Elongation at Break

For the vulcanized rubber sheet for evaluation produced as described above, the elongation at break (EB; unit: %) was measured, in accordance with JIS K6251:2010, by punching out a JIS No. 3 dumbbell shape test piece, and performing the measurement under conditions at room temperature and at a tensile speed of 500 mm/min. For the elongation at break, a larger index value indicates greater elongation at break and thus is preferable.

TABLE 2-1

| | | Standard Example 1 | Working Example 1 | Working Example 2 | Working Example 3 | Working Example 4 | Working Example 5 |
|---|---|---|---|---|---|---|---|
| Production of modified polymer | Raw material styrene-butadiene rubber 1 (oil-extended) | — | 137.5<br>100 | ← <br> ← | ← <br> ← | ← <br> ← | ← <br> ← |
| | Modifier 1 | — | 0.42 | 0.83 | 1.39 | 5.56 | 0.83 |
| | Modifier 2 | — | | | | | |
| | Modification temperature | — | 160° C. | 160° C. | 160° C. | 160° C. | 160° C. |
| | Produced modified polymer (oil-extended) | — | Modified SBR 1 | Modified SBR 2 | Modified SBR 3 | Modified SBR 4 | Modified SBR 2 |
| | Modification ratio of double bonds in modified polymer (mol %) | — | 0.17 | 0.33 | 0.55 | 1.93 | 0.33 |
| Rubber Composition | Solution polymerized SBR 1 (St 40%, Vi 41%, oil extension: 37.5 wt %) | 49.50<br>36 | | | | | |
| | Solution polymerized SBR 2 (St 35%, Vi 45%, oil extension: 37.5 wt %) | 66.00<br>48 | ←<br>48 | ←<br>48 | ←<br>48 | ←<br>48 | 77.00<br>56.00 |
| | BR | 16.00 | ← | ← | ← | ← | 8.00 |
| | Modified SBR 1 | | 49.50<br>36 | | | | |
| | Modified SBR 2 | | | 49.50<br>36 | | | 49.50<br>36.00 |
| | Modified SBR 3 | | | | 49.50<br>36 | | |
| | Modified SBR 4 | | | | | 49.50<br>36 | |
| | P modified SBR | | | | | | |
| | Silica | 70.00 | ← | ← | ← | ← | ← |
| | Carbon black (carbon) | 10.00 | ← | ← | ← | ← | ← |
| | Processing aid | 2.00 | ← | ← | ← | ← | ← |
| | Anti-aging agent | 3.00 | ← | ← | ← | ← | ← |
| | Stearic acid | 2.00 | ← | ← | ← | ← | ← |
| | Wax | 1.00 | ← | ← | ← | ← | ← |
| | Zinc oxide | 2.00 | ← | ← | ← | ← | ← |
| | Silane coupling agent | 9.00 | ← | ← | ← | ← | ← |
| | Oil | 5.00 | ← | ← | ← | ← | ← |
| | Vulcanization accelerator 1 (CZ) | 2.00 | ← | ← | ← | ← | ← |
| | Vulcanization accelerator 2 (DPG) | 1.50 | ← | ← | ← | ← | ← |
| | Sulfur | 1.00 | ← | ← | ← | ← | ← |
| | Amount of modifier introduced to modified polymer in 100 parts by mass of diene-based rubber (part by mass) | 0.00 | 0.15 | 0.30 | 0.50 | 2.00 | 0.3 |
| | Heat build-up (index) | 100 | 95 | 92 | 89 | 83 | 93 |
| | Elongation at break (index) | 100 | 101 | 108 | 103 | 103 | 101 |

TABLE 2-2

|  |  | Working Example 6 | Working Example 7 | Working Example 8 |
|---|---|---|---|---|
| Production of modified polymer | Raw material styrene-butadiene rubber 1 (oil-extended) | 137.5<br>100 | ←<br>← | ←<br>← |
|  | Modifier 1 |  | 0.83 | ← |
|  | Modifier 2 | 5.56 |  |  |
|  | Modification temperature | 160° C. | 160° C. | 160° C. |
|  | Produced modified polymer (oil-extended) | P modified SBR | Modified SBR 2 | Modified SBR 2 |
|  | Modification ratio of double bonds in modified polymer (mol %) | 1.96 | 0.33 | 0.33 |
| Rubber Composition | Solution polymerized SBR 1 (St 40%, Vi 41%, oil extension: 37.5 wt %) |  |  |  |
|  | Solution polymerized SBR 2 (St 35%, Vi 45%, oil extension: 37.5 wt %) | 66.00<br>48 | 86.35<br>62.80 | 60.50<br>44.00 |
|  | BR |  | 1.20 | 20.00 |
|  | Modified SBR 1 |  |  |  |
|  | Modified SBR 2 |  | 49.50<br>36.00 | 49.50<br>36.00 |
|  | Modified SBR 3 |  |  |  |
|  | Modified SBR 4 |  |  |  |
|  | P modified SBR | 49.50<br>36 |  |  |
|  | Silica | 70.00 | ← | ← |
|  | Carbon black (carbon) | 10.00 | ← | ← |
|  | Processing aid | 2.00 | ← | ← |
|  | Anti-aging agent | 3.00 | ← | ← |
|  | Stearic acid | 2.00 | ← | ← |
|  | Wax | 1.00 | ← | ← |
|  | Zinc oxide | 2.00 | ← | ← |
|  | Silane coupling agent | 9.00 | ← | ← |
|  | Oil | 5.00 | ← | ← |
|  | Vulcanization accelerator 1 (CZ) | 2.00 | ← | ← |
|  | Vulcanization accelerator 2 (DPG) | 1.50 | ← | ← |
|  | Sulfur | 1.00 | ← | ← |
|  | Amount of modifier introduced to modified polymer in 100 parts by mass of diene-based rubber (part by mass) | 2.00 | 0.3 | 0.3 |
|  | Heat build-up (index) | 92 | 94 | 92 |
|  | Elongation at break (index) | 94 | 89 | 93 |

The details of each component of the rubber compositions shown in Table 2 above are as follows.

Solution polymerized SBR 1: Nipol NS522, manufactured by Zeon Corporation; solution polymerized styrene-butadiene rubber; weight average molecular weight: 1,360,000; styrene content: 40% by mass; vinyl content: 41 mol %; amount of oil extension: 37.5% by mass Solution polymerized SBR 2: Tufdene 3835, manufactured by Asahi Kasei Corporation; solution polymerized styrene-butadiene rubber; weight average molecular weight: 790,000; styrene content: 35% by mass; vinyl content: 45 mol %; amount of oil extension: 37.5% by mass BR: Nipol BR 1220, manufactured by Zeon Corporation; butadiene rubber; weight average molecular weight: 600,000

Modified SBRs 1 to 4, P modified SBR: SBRs produced as described above

Silica: Zeosil 165GR, manufactured by Rhodia Silica Korea Co., Ltd.

Carbon black (carbon): Seast 9M, manufactured by Tokai Carbon Co., Ltd.; carbon black Processing aid: Struktol Ef44, manufactured by Schill & Seilacher Gmbh & Co.

Anti-aging agent: Santoflex 6PPD, manufactured by Soltia Europe

Stearic acid: Beads Stearic Acid YR, manufactured by NOF Corporation

Wax: SANNOC, manufactured by Ouchi Shinko Chemical Industrial Co., Ltd.

Zinc oxide: zinc oxide; Zinc White No. 3, manufactured by Seido Chemical Industry Co., Ltd.

Silane coupling agent: Si69, manufactured by Evonik-Degussa; bis(3-triethoxysilylpropyl)tetrasulfide Oil: Extract No. 4S, manufactured by Showa Shell Sekiyu K.K.

Vulcanization accelerator 1 (CZ): Noccelar CZ-G, manufactured by Ouchi Shinko Chemical Industrial Co., Ltd.

Vulcanization accelerator 2 (DPG): Soxinol D-G, manufactured by Sumitomo Chemical Co., Ltd.

Sulfur: oil-treated sulfur, manufactured by Karuizawa Refinery Ltd.

Regarding Table 2

As is clear from the results shown in Table 2, Working Examples 1 to 8 exhibited superior low heat build-up compared to that of Standard Example 1 which did not contain the modified polymer.

Furthermore, when Working Examples 1 to 5 were compared for low heat build-up, higher modification ratio of the modified polymer resulted in superior low heat build-up.

In Working Examples 1 to 5, superior low heat build-up and higher elongation at break were achieved compared to those of Standard Example 1. Working Examples 2 to 4 achieved excellent balance between breaking strength and low heat build-up while the high breaking strength was maintained.

On the other hand, Working Example 6 which did not contain a butadiene rubber resulted in lower elongation at break compared to that of Standard Example 1.

Working Example 7, in which the ratio of modified polymer/butadiene rubber was greater than (95/5) [(greater than 95)/(less than 5)], and Working Example 8, in which the ratio of modified polymer/butadiene rubber was less than (68/32) [(less than 68)/(greater than 32)] resulted in lower elongation at break than that of Standard Example 1.

heat build-up. Working Examples 9 and 10 achieved excellent balance between breaking strength and low heat build-up while the high breaking strength was maintained.

TABLE 3

|  |  | Standard Example 2 | Working Example 9 | Working Example 10 | Working Example 11 |
|---|---|---|---|---|---|
| Production of modified polymer | Raw material styrene-butadiene rubber 2 (oil-extended) | — | 137.5 100 | ← ← | ← ← |
|  | Modifier 1 | — | 0.8 | ← | ← |
|  | Modification temperature | — | 160° C. | ← | ← |
|  | Produced modified polymer (oil-extended) | — | Modified SBR 5 | ← | ← |
|  | Modification ratio of double bonds in modified polymer (mol %) | — | 0.18 | ← | ← |
| Rubber Composition | NR | 16.00 | ← | ← | ← |
|  | Solution polymerized SBR 3 (St 37%, oil extension: 37.5 phr) | 98.00 71 | 57.75 42 | 49.00 36 |  |
|  | BR | 13.00 | 13.00 | ← | ← |
|  | Modified SBR 5 |  | 39.90 29 | 48.00 35 | 98.00 71 |
|  | Carbon black (CB) | 20.00 | ← | ← | ← |
|  | Silica | 60.00 | ← | ← | ← |
|  | Stearic acid | 2.00 | ← | ← | ← |
|  | Processing aid | 2.00 | ← | ← | ← |
|  | Anti-aging agent | 3.00 | ← | ← | ← |
|  | Wax | 1.00 | ← | ← | ← |
|  | Silane coupling agent (Si 69) | 4.80 | ← | ← | ← |
|  | Oil | 16.17 | ← | ← | ← |
|  | Zinc oxide | 3.00 | ← | ← | ← |
|  | Sulfur | 1.85 | ← | ← | ← |
|  | Vulcanization accelerator 1 (CZ) | 2.30 | ← | ← | ← |
|  | Vulcanization accelerator 2 (DPG) | 0.65 | ← | ← | ← |
|  | Amount of modifier introduced to modified polymer in 100 parts by mass of diene-based rubber (part by mass) | 0.00 | 0.25 | 0.3 | 0.6 |
|  | Heat build-up (index) | 100 | 95 | 91 | 83 |
|  | Elongation at break (index) | 100 | 102 | 104 | 101 |

The details of each component of the rubber compositions shown in Table 3 above are as follows.

NR: Natural rubber TSR 20

Solution polymerized SBR 3 (St 37%; oil extension: 37.5 wt %): E580, manufactured by Asahi Kasei Chemicals Corporation; solution polymerized styrene-butadiene rubber; weight average molecular weight: 800,000; styrene content: 37% by mass; amount of oil extension: 37.5% by mass BR: same as those in Table 2

Modified SBR 5: SBR produced as described above

Components from carbon black (CB) to vulcanization accelerator 2 (DPG): same as those in Table 2 except the processing aid Processing aid in Table 3: Aktiplast ST, manufactured by Rhein Chemie (Qingdao)

Regarding Table 3

As is clear from the results shown in Table 3, Working Examples 9 to 11 exhibited superior low heat build-up compared to that of Standard Example 2 which did not contain the modified polymer.

In Working Examples 9 to 11, higher elongation at break was achieved compared to that of Standard Example 2.

When Working Examples 9 to 11 were compared, greater amount of the modified polymer resulted in superior low

REFERENCE SIGNS LIST

1 Bead portion
2 Sidewall portion
3 Tire tread portion
4 Carcass layer
5 Bead core
6 Bead filler
7 Belt layer
8 Rim cushion

The invention claimed is:

1. A modified polymer obtained by modifying a styrene-conjugated diene copolymer (A) with a nitrone compound (B),
the modified polymer having a five-membered ring structure represented by formula (4) or (5), represented by the formula:

(4)

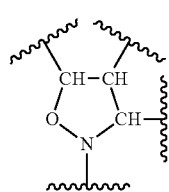

-continued

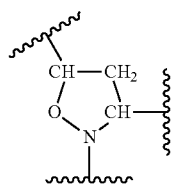
(5)

which is formed by a cycloaddition reaction between a double bond of the styrene-conjugated diene copolymer (A) and a nitrone group of the nitrone compound (B);

a content of styrene units in the styrene-conjugated diene copolymer (A) being 10% by mass or greater;

a proportion of vinyl bonds among all the double bonds contained in the styrene-conjugated diene copolymer (A) being 5 mol % or greater; and wherein the nitrone compound (B) has a carboxy group.

2. The modified polymer according to claim 1, wherein the nitrone compound (B) is at least one type of compound selected from the group consisting of N-phenyl-α-(4-carboxyphenyl)nitrone, N-phenyl-α-(3-carboxyphenyl)nitrone, N-phenyl-α-(2-carboxyphenyl)nitrone, N-(4-carboxyphenyl)-α-phenylnitrone, N-(3-carboxyphenyl)-α-phenylnitrone, and N-(2-carboxyphenyl)-α-phenylnitrone.

3. The modified polymer according to claim 1, wherein the styrene-conjugated diene copolymer (A) is a styrene-butadiene rubber.

4. A rubber composition comprising the modified polymer described in claim 1.

5. The rubber composition according to claim 4, further comprising a diene-based rubber except the modified polymer.

6. The rubber composition according to claim 5, wherein the diene-based rubber except the modified polymer is at least one type selected from the group consisting of butadiene rubbers, aromatic vinyl-conjugated diene copolymers, and natural rubbers.

7. The rubber composition according to claim 6, wherein a mass ratio of the modified polymer to the butadiene rubber (modified polymer/butadiene rubber) is from 95/5 to 68/32.

8. The rubber composition according to claim 6, wherein a mass ratio of the modified polymer to the aromatic vinyl-conjugated diene copolymer [(modified polymer)/(aromatic vinyl-conjugated diene copolymer)] is (10 or greater)/(90 or less).

9. The rubber composition according to claim 6, wherein a mass ratio of the butadiene rubber to the natural rubber (butadiene rubber/natural rubber) is from 20/80 to 70/30.

10. The rubber composition according to claim 5, wherein a content of the modified polymer is 10 parts by mass or greater per 100 parts by mass total of a content of the modified polymer and a content of the diene-based rubber except the modified polymer.

11. The rubber composition according to claim 4, further comprising silica.

12. The rubber composition according to claim 11, wherein a content of the silica is from 8 to 130 parts by mass per 100 parts by mass total of a content of the modified polymer and a content of the diene-based rubber except the modified polymer.

13. A pneumatic tire comprising the rubber composition described in claim 4.

* * * * *